US006780835B2

(12) United States Patent
Perring et al.

(10) Patent No.: US 6,780,835 B2
(45) Date of Patent: Aug. 24, 2004

(54) PERFUME COMPOSITIONS

(75) Inventors: Keith Douglas Perring, Kent (GB); Christopher Francis Clements, Kent (GB); Angus Peter Macmaster, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 10/230,413

(22) Filed: Aug. 29, 2002

(65) Prior Publication Data

US 2003/0096730 A1 May 22, 2003

Related U.S. Application Data

(63) Continuation of application No. 09/529,098, filed as application No. PCT/GB98/03057 on Oct. 9, 1998, now Pat. No. 6,465,420.

(30) Foreign Application Priority Data

Oct. 10, 1997 (GB) ............................................ 9721587

(51) Int. Cl.[7] .................................................. A61K 7/46
(52) U.S. Cl. ............................................ 512/1; 510/101
(58) Field of Search ............................... 512/1; 510/101

(56) References Cited

U.S. PATENT DOCUMENTS

| | | | | |
|---|---|---|---|---|
| 4,304,679 | A | 12/1981 | Hooper et al. | 252/106 |
| 4,604,488 | A | 8/1986 | Fujikura et al. | 568/830 |
| 5,482,635 | A | 1/1996 | Behan et al. | 252/8.8 |
| 5,500,138 | A | 3/1996 | Bacon et al. | 252/8.8 |
| 5,554,588 | A | 9/1996 | Behan et al. | 512/1 |

FOREIGN PATENT DOCUMENTS

| | | |
|---|---|---|
| EP | 0 147 191 | 7/1985 |
| WO | 97/31097 | 8/1997 |

OTHER PUBLICATIONS

Database WP1–Derwent Publication, AN 78–20668A, XP002092224 & JP 53 012432 A, Feb. 3, 1978.

Database WP1–Derwent Publication, AN 94–239062, XP002092225 & JP 06 172781A, Jun. 21, 1994.

*Primary Examiner*—Jill Warden
*Assistant Examiner*—Monique T. Cole
(74) *Attorney, Agent, or Firm*—Morgan Lewis & Bockius LLP

(57) ABSTRACT

A perfume composition which gives good deposition and/or substantially improved deodorant effectiveness on textiles incorporating spandex® fibres. The perfume comprises a mixture of fragrance materials in which at least 60% by weight of the composition comprises fragrance materials drawn from categories I and II.

11 Claims, No Drawings

PERFUME COMPOSITIONS

Application Ser. No. 09/529,098 filed on Jun. 19, 2000. International Application No. PCT/GB98/03057 filed on Oct. 9, 1998 and which designated the U.S.

This invention relates to perfumes, to laundry compositions containing such perfumes, and the use of these compositions to deposit perfume on fabrics.

The use of perfumes in laundry products has been established for many years. Perfume is used to cover base odour and to provide fragrance notes which are attractive or pleasing to the consumer. Generally, it is important that a perfume be able to perform well olfactively at a number of stages, for example, from product 'in the pack', during product use, on damp cloth after laundering and on dry cloth (i.e. after drying the damp cloth). Certain perfumes have the ability to provide deodorant action against body odour, either when directly applied to human skin, or when included in a laundry product. Such perfumes are described in EP-B-3172, U.S. Pat. Nos. 4,304,679, 4,278,658, 4,134, 838, 4,288,341 and 4,289,641, 5,482,635 and 5,554,588.

It is important that sufficient fragrance should be transferred onto the fabric to be perceptible after laundering or (if the perfume has deodorant properties) to yield the deodorant effect.

A number of techniques have been proposed for increasing perfume delivery (to) and/or perfume longevity (on) substrates such as skin, hair, fabric and hard surfaces. This includes the use of fixative materials in the perfume to depress perfume ingredient partial pressures (eg GB 1534231) thereby reducing evaporative loss, and the use of carriers (eg EP 332259) or microcapsules (eg EP 376385) to deliver perfume to fabric. These technologies may increase perfume presence on dry cloth but involve further processing steps and/or material costs.

Compositions aiming to improve retention of "non-volatile" or "enduring" perfume ingredients, respectively, are disclosed in U.S. Pat. No. 5,500,138 and WO-A-97/31097.

At the present time, many garments are made from fabric which contains a mixture of fibres, a proportion of which are elastic, so that the fabric has the ability to stretch and to recover from stretch. Spandex fibres are commonly used for this purpose. The term "spandex" has been adopted as a generic term by the United States Federal Trade Commission to denote a manufactured fibre in which the fibre-forming substance is a long chain synthetic polymer composed of at least 85% of a segmented polyurethane. A discussion of such fibres can be found in "History of Spandex Elastomeric Fibres" by A. J. Ultee, which is a chapter starting at page 278 in *Man-Made Fibres: Their Origin and Development*, edited by R. V. Seymour and R. S. porter, Elsevier 1993. Spandex fibres are also referred to as "elastane" or "elasthane" fibres.

Another discussion of such fibres is found under the heading "Segmented Polyurethanes" at page 613 of *Handbook of Textile Fibres* by J. Gordon Cook, 5th Ed. Merrow Publishing Company 1984. Further description of elastanes and their applications can be found in "Synthesefasern: Grundlagen, Technologie, Verarbeitung und Anwendung", B von Falkei (editor) *Verlag Chemie* (1991). Commercially available elastanes are well known, in particular as sold under the name LYCRA®, a registered trade mark of Dupont de Nemours and Company. Patents relating to such fibres include U.S. Pat. Nos. 5,000,899, 5,288,779 and 5,362,432.

SUMMARY OF THE INVENTION

We have now discovered certain perfumes which give good deposition and/or substantially improved deodorant effectiveness on textiles incorporating spandex fibres.

Broadly, the present invention provides a perfume composition comprising a mixture of fragrance materials in which at least 60% by weight of the composition comprises fragrance materials drawn from the two categories below:

Category I hydroxylic materials which are alcohols, phenols or salicylates, with an octanol/water partition coefficient (P) whose common logarithm ($\log_{10}$ P) is 2.5 or greater, and a gas chromatographic Kovats index (as determined on polydimethylsiloxane as non-polar stationary phase) lying within the range 1050 to 1600.

Category II esters, ethers, ketones or aldehydes, with an octanol/water partition coefficient (P) whose common logarithm ($\log_{10}$ P) is 2.5 or greater, and a gas chromatographic Kovats index (as determined on polydimethylsiloxane as non-polar stationary phase) lying within the range 1300 to 1600.

Particularly preferred are category I materials with a partition coefficient whose common logarithm is 3.0 or greater and a Kovats index of 1100 up to 1600, and category II materials which are ethers, esters, or ketones with a Kovats index of 1350 up to 1600, and possessing one or more rings in their molecular structures.

It is envisaged that the perfumes of this invention will be incorporated into a laundry or other composition for treatment of fabrics. This may be a detergent composition or presoak composition for washing the fabrics or a softening composition for softening the washed fabrics during rinsing and drying.

We have also discovered that the perfume may be incorporated into a composition used for treatment of yarn or new fabric, to provide a perfume benefit on new garments.

The benefit from the perfume compositions may be good deposition or retention of fragrance materials on the fabric. We have observed good deposition of a range of fragrance materials, especially fragrance materials which are of mid-range volatility (i.e. intermediate between the volatile perfume materials used as "top-notes" and the materials of low volatility which are customarily used as base notes in perfumes). These materials of mid-range volatility are often not perceptible on other fabrics such as cotton, polyamide and polyester after washing and drying.

Preferably, the perfume is a deodorant perfume giving a Malodour Reduction Value on cotton of at least 0.25, preferably at least 0.5, in the Malodour Reduction Value test described below and which is generally as given in EP-A-147191 and corresponding U.S. Pat. No. 4,663,068.

With such perfumes we have observed that there is an enhanced deodorant benefit when the fabrics incorporate spandex fibres, compared to conventional fabrics such as cotton, polyamide and polyester without spandex. This can be measured using the Malodour Reduction Value test, modified by varying the test fabric instead of varying the perfume.

The Malodour Reduction Value Test

In this test, the Malodour Reduction Value of a deodorant perfume is measured by assessing its effectiveness, when applied to fabric, in reducing body malodour when the fabric so treated is placed in contact with the axillae (armpits) of a panel of human subjects, and held there for a standard period of is time. From subsequent olfactory evaluation by trained assessors, a Malodour Reduction Value can be calculated so giving a measure of the effectiveness as a deodorant of the perfume under test.

Stage 1 is preparation of the perfume treated fabric.

A fabric is selected for the test and cut into 20 cm×20 cm squares. A control fabric is likewise cut into squares. Both fabrics are then washed in a front-loading drum-type washing machine with a standard unperfumed washing powder containing the following ingredients:

| Ingredient | Parts by weight |
|---|---|
| Sodium dodecylbenzene sulphonate | 9.0 |
| $C_{13-15}$ alcohol 7EO | 4.0 |
| Sodium tripolyphosphate | 33.0 |
| Alkaline sodium silicate | 6.0 |
| Sodium carboxymethyl cellulose | 1.0 |
| Magnesium silicate | 1.0 |
| Ethylenediamine tetraacetic acid | 0.2 |
| Sodium sulphate | 15.0 |
| Water | 10.8 |

The washed pieces of fabric are then rinsed with cold water and finally dried. The fabric squares so obtained represent "untreated" fabric, that is fabric devoid of perfume, other deodorant materials, dressing and other water-soluble substances that subsequently might adversely affect the Malodour Reduction Value Test.

The untreated pieces of fabric are divided into two batches, one of which may receive no further washing treatment and then represents the control fabric in the test. The other batch of fabric pieces is re-washed in the washing machine with the same standard fabric washing powder to which has been added 0.2% by weight of the perfume under test. The perfume treated pieces of fabric are then rinsed with cold water and dried again. The fabric squares so obtained represent "test" fabric, that is fabric onto which the test perfume has been delivered.

When the intention is to test perfume properties, the control and test fabrics are the same, e.g. polyester or cotton shirt fabric and the "untreated" fabric serves as control without further washing. To test deposition on different cloths, the test fabric can differ from the control fabric, and both may be washed with the perfumed washing powder.

Stage 2 is the carrying out of the test. A team of three Caucasian female assessors of age within the range of 20 to 40 years is selected for olfactory evaluation on the basis that each is able to rank correctly the odour levels of the series of standard aqueous solutions of isovaleric acid listed below, and is each is able to assign a numerical score, corresponding to the odour intensity of one of these solutions, to the body malodour of a shirt insert after has been worn in the axillary region by a male subject for a standard period of time.

A panel of 40 human subjects for use in the test is assembled from Caucasian male subjects of age within the range of from 20 to 55 years. By screening, subjects are chosen who develop axillary body malodour that is not unusually strong and who do not develop a stronger body malodour in one axilla compared with the other. Subjects who develop unusually strong body malodour, for example due to a diet including curry or garlic, are not selected for the panel.

For two weeks before the start of the test, the panel subjects are assigned an unperfumed, non-deodorant soap bar for exclusive use when washing and are denied the use of any other type of deodorant or antiperspirant. At the end of this period, the 40 subjects are randomly divided into two groups of 20.

The "test" and "control" fabric pieces are then tacked into 40 clean cotton or polyester-cotton shirts in the underarm region in such a manner that in 20 shirts, the control fabric pieces are attached inside the left underarm region, and the test fabric pieces are attached in the right underarm region. For the remaining 20 shirts, the placing of control and test pieces of fabric is reversed.

The shirts carrying the tacked-in fabric inserts are then worn by the 40 panel members for a period of 5 hours, during which time each panellist performs his normal work function without unnecessary exercise.

After this five hour period, the shirts are removed and the inserts detached and placed in polyethylene pouches prior to assessment by the trained panel of assessors.

The malodour intensity of each fabric insert is evaluated by all three assessors who, operating without knowledge of which inserts are "test" and which are "control" and, without knowing the scores assigned by their fellow assessors, sniff each fabric piece and assign to it a score corresponding to the strength of the odour on a scale from 0 to 5, with 0 representing no odour and 5 representing very strong odour.

Standard aqueous solutions of isovaleric acid which correspond to each of the scores 1, 2, 3, 4 and 5 are provided for reference to assist the assessors in the malodour evaluation. These are shown below:

| Score | Odour level | Concentration of aqueous isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each fabric piece are averaged. The average score of the "test" fabric pieces is deducted from the average score of the "untreated" control fabric pieces to give a Malodour Reduction Value.

As a check that the selection of panel subjects is satisfactory for operation of the test, the average score with untreated fabric pieces should be between 2.5 and 3.0.

Preferred deodorant perfumes are those which have a Malodour Reduction Value of at least 0.50, or 0.70, or 1.00. The higher the minimum value, the more effective is the perfume as a deodorant as recorded by the assessors in the Malodour Reduction Value Test. It has also been noted that consumers, who are not trained assessors, can detect by self-assessment a noticeable reduction in malodour on soiled fabric such as shirts and underclothes where the Malodour Reduction Value is at least 0.30, so the higher the Malodour Reduction Value above this figure, the more noticeable is the deodorant effect.

Perfume Materials and Preferences

As mentioned above, the perfumes of this invention must contain a number of fragrance materials specified by the presence of chemical structural groups, octanol/water partition coefficient (P) and Kovats index.

The octanol-water partition coefficient (or its common logarithm 'log P') is well known in the literature as an indicator of hydrophobicity and water solubility (see Hansch and Leo, *Chemical Reviews*, 526 to 616, (1971), 71; Hansch, Quinlan and Lawrence, *J. Organic Chemistry*, 347 to 350 (1968), 33). Where such values are not available in the literature they may be measured directly, or approximately estimated using mathematical algorithms. Software providing such estimations are available commercially, for example 'Log P' from Advanced Chemistry Design Inc.

A requirement for $\log_{10}$ P of 2.5 or more calls for materials which are somewhat hydrophobic.

Kovats indices are calculated from the retention time in a gas chromatographic measurement referenced to the retention time for alkanes [see Kovats, *Helv.Chim.Acta* 41, 1915 (1958)]. Indices based on the use of a non-polar stationary phase have been used in the perfumery industry for some years as a descriptor relating to the molecular size and boiling point of ingredients. A review of Kovats indices in the perfume industry is given by T Shibamoto in "Capillary Gas Chromatography in Essential Oil Analysis", P Sandra and C Bicchi (editors), Huethig (1987), pages 259 to 274. A common non-polar phase which is suitable is 100% dimethyl polysiloxane, as supplied for example under a variety of tradenames such as HP-1 (Hewlett-Packard) CP Sil 5 CB (chrompack), OV-1 (Ohio Valley) and Rtx-1 (Restek).

The perfume materials fall into two sets referred to as categories I and II, differing in their minimum values of Kovats index.

Category I includes alcohols of general formula ROH where the hydroxyl group may be primary, secondary or tertiary, and the R group is an alkyl or alkenyl group, optionally branched or substituted, cyclic or acyclic, Such that ROH has partition coefficient and Kovats properties as defined above. Typically this group comprises monofunctional alkyl or arylalkyl alcohols with molecular weight falling within the rage 150 to 230.

Category I also includes phenols of general formula ArOH, where the Ar group denotes a benzene ring which may be substituted with one or more alkyl or alkenyl groups, or with an ester grouping —$CO_2A$, where A is a hydrocarbon radical. As at the ortho position relative to the hydroxy group, the compound is a salicylate. ArOH has partition coefficient and Kovats index as defined above. Typically this group comprises monohydroxylic phenols with molecular weight falling within the range 150 to 210.

Ingredients which are particularly preferred are those with a partition coefficient of 1000 or more, i.e. $\log_{10}$ P of 3 or more, and a Kovats parameter of 1100 up to 1600.

Some examples of hydroxylic ingredients which fulfil the above criteria for category I are listed as a table below. Materials which are in the preferred sub-set are marked with an asterisk. Semitrivial names are those used in standard texts known within the perfume industry, particularly: *Common Fragrance and Flavor Materials* by Bauer, Garbe and Surburg, VCH Publ., 2nd edition (1990), and *Perfume and Flavour Materials*, Steffen Arctander, published in two volumes by the author (1969).

| Examples of fragrance materials in category I |
|---|
| 1-(2'-tert-butylcyclohexyloxy)-butan-2-ol* |
| 3-methyl-5-(2',2',3'-trimethylcyclopent-3-enyl)-pentan-2-ol* |
| 4-methyl-3-decen-5-ol* |
| amyl salicylate* |
| 2-ethyl-4(2',2',3'-trimethylcyclopent-3'-enyl)-but-2-enol* (Bangalol, TM) |
| borneol* |
| carvacrol* |
| citronellol* |
| 9-decenol* |
| dihydroeugenol* |
| dihydrolinalol* |
| dihydromyrcenol* |
| dihydroterpineol* |
| eugenol |
| geraniol* |
| isoamyl salicylate* |
| isobutyl salicylate* |

-continued

| Examples of fragrance materials in category I |
|---|
| Isoeugenol* |
| linalol |
| menthol* |
| nerolidol* |
| nerol* |
| para tert-butyl cyclohexanol* |
| phenoxanol* |
| terpineo |
| tetrahydrogeraniol* |
| tetrahydrolinalol |
| tetrahydromyrcenol |
| thymol* |
| 2-methoxy-4-methylphenol (Ultravanil, TM) |
| (4-isopropylcyclohexyl)-methanol* |

Category II is esters, ketones, nitriles, aldehydes or ethers which have an octanol-water partition coefficient whose common logarithm ($\log_{10}$ P) is at least 2.5, and a Kovats index of 1300 up to 1600 (non-polar phase).

Ingredients of Category II are of general formula RX, where X may be in a primary, secondary or tertiary position and is one of the following groups: —COA, —OA, —$CO_2A$, —CN or —CHO. R and A are hydrocarbon residues, cyclic or non-cyclic and optionally substituted. In some forms of this invention, category II excludes any material with a free hydroxy group, so that where a hydroxyl group is present, the material should be considered only for Category I membership. Typically, the materials of Category II are monofunctional compounds with molecular weights in the range 160 to 230.

Ingredients which are particularly preferred are those with a Kovats parameter falling within the range 1350 up to 1600, and possessing a molecular structure containing a ring, such as phenyl or cycloalkyl.

A number of fragrance materials which fulfil the above criteria for category II are listed in the table below. Materials which are in the preferred sub-set are marked with an asterisk.

| Examples of fragrance materials in category II |
|---|
| 1-methyl-4-(4-methyl-3-pentenyl)-3-cyclohexene-1-carbaldehyde* |
| 1-(5',5'-dimethylcyclohexenyl)-pent-en-1-one* |
| 2-heptyl cyclopentanone* |
| 2-methyl-3-(4'-tert-butylphenyl)propanal |
| 2-methylundecanal |
| 2-undecenal |
| 2,2-dimethyl-3-(4'-ethylphenyl)-propanal |
| 3-(4'-isopropylphenyl)-2-methylpropanal |
| 4-methyl-4-phenylpent-2-yl acetate* |
| allyl cyclohexyl propionate* |
| allyl cyclohexyloxyacetate* |
| amyl benzoate* |
| methyl ethyl ketone trimers (Azarbre, TM) |
| benzophenone* |
| 3-(4'-tert-butylphenyl)-propanal (Bourgeonal, TM) |
| caryophyllene* |
| cis-jasmone* |
| citral diethyl acetal |
| citronellal diethyl acetal |
| citronellyl acetate |
| phenylethyl butyl ether (Cressanther, TM) |
| damascone, alpha-* |
| damascone, beta-* |
| damascone, delta-* |
| decalactone, gamma-* |
| dihydro isojasmonate* |

-continued

| Examples of fragrance materials in category II |
|---|
| dihydrojasmone* |
| dihydroterpinyl acetate |
| dimethyl anthranilate* |
| diphenyl oxide* |
| dodecanal |
| dodecen-2-al |
| dodecane nitrile |
| 1-ethoxy-1-phenoxyethane (Efetaal, TM) |
| 3-(1'-ethoxyethoxy)-3,7-dimethylocta-1,6-diene (Elintaal Forte (TM) |
| 4-(4'-methylpent-3'-enyl)-cyclohex-3-enal (Empetaal, TM) |
| ethyl tricyclo[5.2.1.0-2,6-]decane-2-carboxylate* |
| 1-(7-isopropyl-5-methylbicyclo(2.2.2)oct-5-en-2-yl)-1-ethanone* (Felvinone, TM) |
| allyl tricyclodecenyl ether* (Fleuroxene, TM) |
| tricyclodecenyl propanoate* (Florocyclene, TM) |
| gamma-undecalactone* |
| tricyclodecenyl isobutyrate* (Gardocyclene, TM) |
| geranyl acetate |
| hexyl benzoate* |
| ionone alpha* |
| ionone beta* |
| isobutyl cinnamate* |
| isoeugenyl acetate* |
| 2,2,7,7-tetramethyltricycloundecan-5-one* (Isolongifolanone, TM) |
| tricyclodecenyl acetate* (Jasmacyclene, TM) |
| 2-hexylcyclopentanone (Jasmatone, TM) |
| 4-acetoxy-3-pentyltetrahydropyran* (Jasmopyrane, TM) |
| ethyl 2-hexylacetoacetaet (Jessate, TM) |
| 8-isopropyl-6-methylbicyclo(2.2.2)oct-5-ene-2-carbaldehyde (Maceal, TM) |
| methyl 4-isopropyl-1-methylbicyclo[2.2.2] oct-5-ene-2-carboxylate |
| methyl cinnamate |
| alpha iso methyl ionone* |
| methyl naphthyl ketone* |
| nerolin |
| nonalactone gamma |
| nopyl acetate* |
| para tert-butyl cyclohexyl acetate |
| 2,4-dimethyl-6-phenyldihydroxypyran* (Pelargene, TM) |
| phenoxyethyl isobutyrate* |
| phenylethyl isoamyl ether* |
| phenylethyl isobutyrate* |
| tricyclodecenyl pivalate* (Pivacyclene, TM) |
| phenylethyl pivalate* (Pivarose, TM) |
| phenylacetaldehyde hexylene glycol acetal* |
| 2,4-dimethyl-4-phenyltetrahydrofuran (Rhubafuran, TM) |
| rose acetone* |
| terpinyl acetaet |
| yara* |
| (4-isopropylcyclohexadienyl)ethyl)formate |

Selection of a combination of fragrance materials to give a deodorant effect is explained in patents such as U.S. Pat. No. 4,304,679 referred to earlier. Further systems of selection are given in U.S. Pat. Nos. 5,482,635 and 5,554,588 also mentioned above.

Such selections can be carried out using materials with preferred values of partition coefficient and Kovats index as discussed above.

The perfume compositions of this invention can deliver fragrance or, with appropriate perfume a deodorant benefit, to a range of fabrics, but the benefit is particularly pronounced on fabrics containing spandex fibres.

The polymer which is spun into spandex fibres is a segmented polyurethane, that is a copolymer incorporating polyurethane linkages. The polymer generally contains so-called soft (i.e. lower melting) segments which may be polyalkylene ethers or polyesters and so-called hard (i.e. higher melting) segments which are portions derived from the reaction of an isocyanate and a chain extender which is typically a diamine.

The soft segments may be poly(tetramethylene)ethers, possibly containing substituted tetramethylene glycol residues as described in U.S. Pat. No. 5,000,699. Organic diisocyanates which may be used include conventional diisocyanates, such as diphenylmethane-4,4'-diisocyanate, also known as methylene-bis(4-phenylisocyanate) or "MDI", 2,4-tolylene diisocyanate, methylene-bis(4-cyclohexylisocyanate), isophorone diisocyanate, tetramethylene-p-xylylene diisocyanate, and the like. MDI is preferred.

Chain extenders used in producing the hard segment of the fibres preferably include one or more of ethylenediamine (EDA), 1,3-propylenediamine, 1,4-cyclohexanediamine, hydrogenated m-phenylenediamine (HPMD), 2-methylpentamethylene diamine (MPMD) and 1,2-propylene diamine. More preferably, the chain extender is one or more of ethylenediamine, 1,3-propylenediamine, and 1,4-cyclohexanediamine, optionally mixed with HPMD, MPMD and/or 1,2-propylenediamine.

Spandex fibres with poly(tatramethylene)ethers as the soft segments are marketed by Dupont de Nemours International S.A. under the registered trade mark LYCRA® of Dupont de Nemours and Company.

Spandex fibres are generally mixed with other fibres such as cotton, polyamide, wool, polyester and acrylics and made into yarn which is then made into fabric. The contents of spandex fibres is usually in a range from 0.5% by weight of the yarn or fabric up to 50%, more usually from 1% to 30% by weight of the yarn or fabric.

A wide range of garments may contain spandex fibres in the fabric, including active sports wear, intimate apparel, hosiery and a variety of ready to wear casual clothing.

Fabric Treatment Compositions

Perfume compositions of the invention may be incorporated into fabric treatment products for use in washing, rinsing drying or other treatment of fabrics. Such a product may be any of:

- a detergent composition for fabric washing,
- a pretreatment composition for application to selected areas of a garment prior to washing,
- a pretreatment composition used in the soaking of entire garments prior to washing,
- a rinse conditioner composition for softening washed fabrics during a rinsing step,
- an additive composition for use jointly with any of the above,
- a fabric conditioning article intended to be placed with fabrics during drying, or
- a spray for application directly to dry garments.

Such products can take a variety of forms including powders, bars, sticks, tablets, mousses, gels, liquids, sprays, and also fabric conditioning sheets to be placed with fabrics in a tumble dryer. The amount of perfume in such products may lie in a range from 0.1% to 10% by weight of thereof. The incorporation of perfume into products of these types is known, and existing techniques may be used for incorporating perfume for this invention. It may be possible to incorporate perfume directly into a product, but another possibility is, to absorb the perfume on a carrier material and then admix the perfume-plus-carrier-mixture into the fabric treatment product. This approach may notably be used with a solid fabric treatment product and an inert particulate carrier.

A detergent composition to be perfumed with a perfume composition according to this invention will normally contain a detersive surfactant in an amount from 2% to 50%, preferably 5 to 40% by weight of the composition, and a detergency builder in an amount from 5% to 80% by weight of the composition. The balance of the composition, if any, may include various ingredients known for inclusion in fabric washing detergents, including bleaching materials. Surfactants may be one or more soap or non-soap anionic, nonionic, cationic, amphoteric or zwitterionic surfactants, or combinations of these. Preferred surfactants which can be used are soaps and synthetic non-soap anionic and nonionic compounds. Mixtures of surfactants, for example mixed anionic or mixed anionic and nonionic compounds, are frequently used in detergent compositions.

Detergency builders are materials which function to soften hard water by solubilisation or other removal of calcium and to a lesser extent magnesium salts responsible for water hardness. The commonest water soluble inorganic builder is sodium tripolyphosphate. A further water soluble inorganic builder compound is sodium carbonate which is generally used in conjunction with a seed crystal to accelerate the precipitation of calcium carbonate. Common insoluble inorganic detergency builders are zeolites and layered silicates. Organic detergency-builders such as sodium citrate and polyacrylate can also be used.

Some detergent compositions, usually liquids, are formulated to contain from 5 to 50 wt % surfactant but little or no detergency builder.

Other ingredients which are customarily included in a detergent composition, although not necessarily all together, include alkaline silicate, peroxygen or chlorine bleaches, soil release agents, heavy metal sequestrants, anti-redeposition agents such as sodium carboxymethyl cellulose, enzymes enzyme stabilisers, fabric softening agents including softening clays, fluorescent brighteners, antifoam agents or conversely foam boosters and filler such as sodium sulphate.

Pretreatment compositions for soaking of soiled fabrics prior to the main washing step may contain 5 to 80 wt % by weight detergency builder with little or no surfactant. Such compositions frequently include enzymes.

The amount of perfume in a detergent composition or a presoak composition is likely to lie in a range from 0.1 to 2% by weight of the composition.

A fabric conditioning composition may contain from 1% to 40% by weight of a fabric conditioning agent which may be a fabric softening agent, but may contain higher levels in a very concentrated product. Fabric softening agents are frequently nonionic or cationic organic compounds incorporating at least one alkyl, alkenyl or acyl group of 8 or more carbon atoms. These include, but are not limited to:

(i) quaternary ammonium and imidazolinium compounds and corresponding tertiary amines and imidazolines incorporating at least one, preferably two, C8 to C30 alkyl or alkenyl groups; also including alkyl groups containing, ether, ester, carbonate or amide linkages, ethoxylated derivatives and analogues of such compounds and also including compounds with more than one tertiary or quaternary nitrogen atom, (ii) aliphatic alcohols, esters, amines or carboxylic acids incorporating a C8 to C30 alkyl, alkenyl or acyl group, including esters of sorbitan and of polyhydric alcohols, (iii) silicones, mineral oils and polyols such as polyethylene glycol.

A number of fabric conditioning compounds are set out in U.S. Pat. No. 4,137,180, and EP-A-239910.

Fabric conditioning compositions for addition to a rinse liquid are frequently in the form of aqueous dispersions of the conditioning agent. They can also be made in the form of powders.

The amount of perfume in such conditioning liquids and powders is usually 0.1% to 2% by weight. Preferred levels can vary depending on the concentration of softening agent and requirements of the market.

The amount of perfume in very concentrated fabric conditioners may lie in the broader range 0.1% to 10% by weight, preferably 2% to 8% by weight.

A fabric conditioning sheet is intended to be placed with damp, rinsed, laundry in a tumble dryer. Such a product contains a fabric conditioner, which may be a nonionic compound as mentioned above, soap and/or fatty acid, and which melts at temperatures encountered in a tumble dryer. This is carried on a porous sheet Silicone oil may be included. The amount of perfume incorporated in such a product is usually from 2% to 10% of the product and frequently from 2% or 4% to 7% or 8% by weight of the product.

Another form of product for the treatment of fabrics is a carrier liquid containing perfume and packaged in an applicator which delivers the composition as a spray. Such a spray may be marketed as a "refreshing spray" for garments. In such a product, the content of perfume will generally lie in a range from 0.1% to 10% by weight of the liquid composition.

A further possibility is that the perfume is used in the treatment of yarn, or in the "finishing" of new fabric. This is a step in the wet processing of fabrics to improve hand or surface appearance of fabric. The fabric will typically be treated in an aqueous treatment bath containing fabric softener to deposit at a level of up to 3% by weight of the fabric. Perfume according to this invention may be included in the bath to deposit at a level of 0.001% to 1% by weight of the fabric.

EXAMPLE 1

A mixture of perfume ingredients was prepared and added to an unperfumed, but otherwise conventional, laundry detergent powder, to provide a perfume concentration of 0.5% by weight.

The perfumed powder was used to wash test cloths which had not previously been treated with any perfume. These were either all cotton, or 95% cotton with 5% spandex. After washing, the cloths were rinsed and then line dried overnight.

The perfume was extracted from the dry cloths with organic solvent, and the content of the perfume ingredients in the solvent extracts was determined by gas chromatography. If the concentration of an ingredient extracted from the spandex containing cloth was greater than from the all-cotton cloth by a factor of 5 to 20, the result was coded as a medium enhancement (M). If the concentration was greater by 20 or more, it was coded high(H) and if less than 5 or not measurable, it was coded(L).

The results obtained were as follows:

| Ingredient | K* | logP** | Enhancement | Category |
|---|---|---|---|---|
| Boisambrene Forte | 1714 | 5.5 | M | — |
| Benzyl acetone | 1206 | 2.0 | M | — |
| Citronellol | 1209 | 3.6 | H | I |
| 2,6-Dimethyl-heptan-2-ol | 975 | 2.9 | L | — |
| Jasmacyclene | 1394 | 2.9 | H | II |
| Methyl salicylate | 1167 | 2.3 | L | — |
| 2-Phenylethanol | 1087 | 1.4 | L | — |

-continued

| Ingredient | K* | logP** | Enhancement | Category |
|---|---|---|---|---|
| Terpinyl acetate | 1331 | 4.0 | H | II |
| Tetrahydrogeraniol | 1180 | 3.6 | H | I |
| Tetrahydrolinalol | 1083 | 3.5 | H | I |
| Tonalid | 1840 | 6.4 | M | — |
| Yara | 1416 | 3.2 | H | II |

*Measured on OV1 phase using capillary gc
**Measured or estimated using 'logP' software from ACD Inc.

EXAMPLE 2

Two perfume compositions embodying this invention and a comparative composition contained perfume ingredients in the specified categories, as follows:

| Perfume | Category I | Category II | Other |
|---|---|---|---|
| A | 35.1 | 46.6 | 18.3 |
| B | 41.8 | 43.8 | 14.4 |
| C | 27.6 | 29.0 | 43.4 |

These were used in the procedure of the Malodour Reduction Value test, as above, using test cloths which were 95% cotton 5% spandex. For the control, unperfumed washing powder was used to wash all-cotton test cloths. The following results were obtained:

| | Perfume A | Perfume B | Perfume C |
|---|---|---|---|
| Average panel score: | 1.04 | 1.29 | 1.57 |
| Control panel score: | 2.46 | 2.46 | 2.46 |
| Malodour Reduction Value: | 1.42 | 1.17 | 0.89 |
| Malodour Reduction Value as % of control score: | 57.7 | 47.4 | 36.1 |

What is claimed is:

1. A perfume composition which is a mixture of fragrance materials characterized by containing at least 60 wt % of the composition of ingredients which are fragrance materials selected from both of Categories I and II;

Category I) hydroxylic materials which are alcohols, phenols or salicylates, with an octanol/water partition coefficient (P) whose common logarithm ($log_{10}P$) is 3.0 or greater, and a gas chromatographic Kovats index (as determined on polydimethylsiloxane as non-polar silicone stationary phase) lying within the range 1100 to 1600, and Category II) esters, ethers, nitriles, ketones or aldehydes, with an octanol/water partition coefficient (P) whose common logarithm ($log_{10}P$) is 2.5 or greater, and a gas chromatographic Kovats index (as determined on polydimethylsiloxane as non-polar silicone stationary phase) lying within the range 1300 to 1600, said composition containing at least 33 wt % of fragrance materials selected from Category I.

2. A perfume composition according to claim 1 including more than one fragrance material from at least one of said Categories I and II.

3. A perfume composition according to claim 2 including at least three fragrance materials from at least one of said Categories I and II.

4. A perfume composition according to claim 1 containing at least 20 wt % of the composition of fragrance material from Category II.

5. A perfume composition according to claim 4 containing at least 30 wt % of fragrance material from Category II.

6. A perfume composition according to claim 1 wherein the fragrance materials in Category I are selected from the group consisting of 1-(2'-tert-butylcyclohexyloxy)-butan-2-ol
3-methyl-5-(2',2',3'-trimethylcyclopent-3-enyl)-pentan-2-ol
4-methyl-3-decen-5-ol
amyl salicylate
2-ethyl-4(2',2',3'-trimethylcyclopent-3'-enyl)-but-2-enol (Bangalol, TM)
Borneol
Carvacrol
Citronellol
D-decenol
Dihydroeugenol
Dihydrolinalol
Dhydroterpineol
Geraniol
isoamyl salicylate
isobutyl salicylate
Isoeugenol
Menthol
Nerolidol
Nerol
para tert-butyl cyclohexanol
Phenoxanol
Tetrahydrogeraniol
Thymol
(4-isopropylcyclohexyl)-methanol.

7. A perfume composition according to claim 1 wherein the fragrance materials in Category II are selected from the group consisting of:

1-methyl-4-(4-methyl-3-pentenyl)-3-cyclohexene-1-carbaldehyde
1-(5',5'-dimethylcyclohexenyl)-pent-en-1-one
2-heptyl cyclopentanone
2-methyl-3-(4'-tert-butylphenyl)propanal
2-methylundecanal
2-undecenal
2,2-dimethyl-3-(4'-ethylphenyl)-propanal
3-(4'-isopropylphenyl)-2-methylpropanal
4-methyl-4-phenylpent-2-yl acetate
allyl cyclohexyl propionate
allyl cyclohexyloxyacetate
amyl benzoate
methyl ethyl ketone trimers (Azarbre, TM)
Benzophenone
3-(4'-tert-butylphenyl)-propanal (Bourgeonal, TM)
Caryophyllene
cis-jasmone
citral diethyl acetal
citronellal diethyl acetal
citronellyl acetate
phenylethyl butyl ether (Cressanther, TM)
damascone, alpha-
damascone, beta-
damascone, delta-
demascone, gamma-
dihydro isojasmonate
Dihydrojasmone
dihydroterpinyl acetate
dimethyl anthranilate
diphenyl oxide
Dodecanal
dodecen-2-al
dodecane nitrile
1-ethoxy-1-phenoxyethane (Efetaal, TM)
3-(1'-ethoxyethoxy)-3,7-dimethylocta-1,6-diene (Elintaal Forte (TM)
4-(4'-methylpent-3'-enyl)-cyclohex-3-enal (Empetaal, TM)

-continued

| |
|---|
| ethyl tricyclo[5.2.1.0-2,6~]decane-2-carboxlate |
| 1-(7-isopropyl-5-methylbicyclo[2.2.2.]oct-5-en-2-yl)-1-ethanone (Felvinone, TM) |
| allyl tricyclodecenyl ether (Fleuroxene, TM) |
| tricyclodecenyl propanoate (Florocyclene, TM) |
| gamma-undecalactone |
| tricyclodecenyl isobutyrate (Gardocyclene, TM) |
| geranyl acetate |
| hexyl benzoate |
| ionone alpha |
| ionone beta |
| isobutyl cinnamate |
| isoeugenyl acetate |
| 2,2,7,7-tetramethyltricycloundecan-5-one (Isolongifolanone, TM) |
| tricyclodecenyl acetate (Jasmacyclene, TM) |
| 2-hexylcyclopentanone (Jasmatone, TM) |
| 4-acetoxy-3-pentyltetrahydropyran (Jasmopyrane, TM) |
| ethyl 2-hexylacetoacetate (Jessate, TM) |
| 8-isopropyl-6-methylbicyclo[2.2.2]oct-5-ene-2-carbaldehyde (Maceal, TM) |
| methyl 4-isopropyl-1-methylbicyclo[2.2.2]oct-5-ene-2-carboxylate |
| methyl cinnamate |
| alpha iso methyl ionone |
| methyl naphthyl ketone |
| Nerolin |
| nonalactone gamma |
| nopyl acetate |
| para tert-butyl cyclohexyl acetate |
| 2,4-dimethyl-6-phenyldihydroxypyran(Pelargene, TM) |
| phenoxyethyl isobutyrate |
| phenylethyl isoamyl ether |
| phenylethyl isobutyrate |
| tricyclodecenyl pivalate (Pivacyclene, TM) |
| phenylethyl pivalate (Pivarose, TM) |
| phenylacetaldehyde hexylene glycol acetal |
| 2,4-dimethyl-4-phenyltetrahydrofuran (Rhubafuran, TM) |
| rose acetone |
| terpinyl acetate |
| Yara |
| (4-isopropylcyclohexadienyl)ethyl formate. |

8. A perfume composition according to claim 1 which is deodorant perfume having a malodour reduction value of from 0.5 to 3.0 as measured by the Malodour Reduction Test herein, carried out using 100% cotton fabric for both the test and the control pieces.

9. A perfume composition according to claim 1 wherein the Category I materials are selected from the group consisting of monofunctional alkyl and arylalkyl alcohols of mw 150 to 230.

10. A perfume composition according to claim 1 wherein Category II materials have a Kovats index of 1350 to 1600 and a molecular structure containing a ring.

11. A perfume composition according to claim 1 wherein Category II materials have a Kovats index of 1350 to 1600.

* * * * *